United States Patent [19]

Stuart et al.

[11] Patent Number: 5,546,937
[45] Date of Patent: Aug. 20, 1996

[54] OBTURATOR AND TRACHEOSTOMY TUBE CONTAINING THE OBTURATOR

[76] Inventors: J. Michael Stuart, 24182 Elrond La., Lake Forest, Calif. 92630; Jeff G. Uding, 27039 Pacific Ter., Mission Viejo, Calif. 92692

[21] Appl. No.: 166,472

[22] Filed: Dec. 13, 1993

[51] Int. Cl.$^6$ .................................................. A61M 16/00
[52] U.S. Cl. .............................. 128/207.15; 128/200.26; 128/207.14
[58] Field of Search .................... 128/200.26, 207.14, 128/207.15

[56] References Cited

U.S. PATENT DOCUMENTS

| | | | |
|---|---|---|---|
| 3,794,041 | 2/1974 | Frei et al. ................................ | 128/348 |
| 4,134,405 | 1/1979 | Smit ....................................... | 128/303 R |
| 4,315,509 | 2/1982 | Smit ....................................... | 128/303 R |
| 4,796,607 | 1/1989 | Allred, III et al. ........................ | 128/4 |
| 4,850,351 | 7/1989 | Herman et al. ......................... | 128/303.1 |
| 4,955,384 | 9/1990 | Taylor et al. ............................ | 128/657 |
| 5,003,989 | 4/1991 | Taylor et al. ............................ | 128/772 |
| 5,042,475 | 8/1991 | LaBombard ........................... | 128/207.14 |
| 5,222,487 | 6/1993 | Carr et al. ............................... | 128/200.26 |

*Primary Examiner*—Edgar S. Burr
*Assistant Examiner*—Aaron J. Lewis

[57] ABSTRACT

A plastic obturator suitable for use in a tracheostomy tube comprising a handle at its proximal end, a bullet-like shaped tip at its distal end, and an outer cannula supporting body between the handle and the tip, which outer cannula supporting body contains sectionalized flex points and laterally extending supporting surfaces along its length. Also described is a tracheostomy tube, preferably one that is flexible, containing the plastic obturator of the invention.

9 Claims, 5 Drawing Sheets

OBTURATOR AND TRACHEOSTOMY TUBE CONTAINING THE OBTURATOR

BRIEF DESCRIPTION OF THE INVENTION

The invention relates to a flexible obturator of a length sufficient to allow it to extend the length of a tracheostomy tube, i.e., from the proximal to the distal ends thereoff and curving to the shape of the tracheostomy tube. The obturator of the invention possesses a handle at its proximal end and a tip at its distal end, and a plurality of interbonded protrusion and bendable shaft sections sequentially alternating from the handle to the tip. The protrusions extend from obturator's centered elongated longitudinal axis and make contact or come close to making contact with the interior wall of the tracheostomy tube when the obturator is inserted into the tracheostomy tube. Each protrusion is separated from the other by a bendable shaft section and each bendable shaft section is separated by a protrusion. Each bendable shaft section terminates with connections to the protrusions to which it is associated. The distal end of the obturator possesses means for smooth entry of the tracheostomy tube within which it is situated into the trachea. The invention relates to a flexible obturator lodged within a tracheostomy tube possessing flexible walls.

BACKGROUND TO THE INVENTION

Cannula tracheostomy tubes are inserted into the trachea with the assistance of an obturator. The typical obturator has a curved rigid shaft that conforms to the curvature of the cannula within which it is inserted. The obturator is provided with a smooth rounded tip that conforms to the distal opening of the cannula thereby providing a smooth end to the cannula. The function of the obturator is to block the distal opening of the cannula with a smooth surface that facilitates the inserting of the tracheostomy tube into the trachea without appreciably, or to any extent, traumatizing the lining of the trachea.

The conventional shaft of the obturator is angle-ribbed with the ribs extending longitudinally of the shaft's axis. This gives strength to the shaft but also makes the shaft very rigid. As a result, the cannula is assured of being rigid and such rigidity adds to the discomfort to the patient in the insertion of the tracheostomy tube.

Conventional obturators for flexible trach tubes have been made from flat strips of flexible plastic. These obturators can exhibit some severe problems associated with the interaction of the flat strip geometry with the round bore of the trach tube. The flat strip works by engaging the side wall of the tube to position the tip of the obturator in the proper position. However, the flat strip has to contact the wall of the trach tube to maintain its position near the centerline of the trach tube. The contact angle is very undesirable and forms a mechanical wedge of sorts. Since the flat obturator tends to act as a flat spring, it tends to deflect to form a bow shape when forces are applied to the ends.

When the obturator is placed into the trach tube, a frictional force is seen. This frictional force will tend to start the bowing. The bowing will tend to increase with more insertion as the trach tube typically has a curve formed into it in the first place. The bowing causes the flat strip to be pushed into the mechanical wedge as mentioned above. If the coefficient of friction is high enough, this wedging can cause higher insertion force which compounds the wedging problem. In essence, the insertion force will become higher because of the interaction of the materials and the configuration. At an extreme condition, with high friction, this system could constitute a self locking brake and keep the obturator from ever being completely inserted through the trach tube. In addition, the conventional flat strip obturator provides no support for the tracheostomy tube to prevent collapse except on the axis that is coplanar with the plane of the strip of material.

A second type of conventional obturator consists of a small flexible shaft that can bend with two degrees of freedom. While such an obturator can be rigid enough to support the tip, it is difficult, if not impossible, to keep the axis of the obturator coaxial with the axis of the tracheostomy tube. The obturator shaft could follow the inside or the outside wall of the trach tube which have considerably different lengths. This leads to a high variability of locating the tip within the tip of the tracheostomy tube. In addition, such an obturator would provide no support for the walls of the tube during insertion.

A modification of a conventional shaft is described in U.S. Pat No. 5,042,475, patented Aug. 27, 1991. In the description of the obturator of the patent, the shaft of the obturator is a single flat strip that acts like a spring that is dampened in its flexibility by protrusions extending from the surface of the flat strip. The tendency to cause a locking action is diminished by the contact of the protrusions with the wall of the trach tube at a right angle to the potential wedging action. Consequently, the device described in the patents should exhibit lower insertion force and better positioning of the tip than the conventional flat strip obturator. In addition, this design does support the walls of the trach tube during insertion.

There is a desire to make tracheostomy tubes more flexible to afford the patient more comfort. The increased comfort comes from the flexible tracheostomy tube confirming to the patient's anatomy with a low degree of force. The obturator in U.S. Pat 5,042,475 is still essentially rigid in the plane of the main feature of the device, the flat strip that supports the tip and the protrusions. The device has only one degree of freedom for bending. While the device should decrease the insertion force, the rigidity from the flat strip is counterproductive to achieving maximum patient comfort.

There is a need for an obturator that is flexible in two degrees of freedom for bending for patient comfort and is still fairly rigid along is primary axis to position the tip. There is also a need for an obturator that can accomplish the bending while still maintaining accurate coaxial alignment with the associated tracheostomy tube to accurately position the tip of the obturator, that can meet the criteria above and support the walls of the tracheostomy tube during insertion. And finally, there is a need for an obturator that can be used without regard for the rotational alignment of the obturator with respect to the tracheostomy tube. Satisfying these needs are objectives of this invention.

THE INVENTION

This invention relates to a novel obturator with sectionalized flexibility for insertion in tracheostomy tube, especially an obturator designed for adult, neonatal and pediatric tracheotomy applications. This invention relates to an obturator of a length sufficient to allow it and its central longitudinal axis to extend the length of a cylindrical tracheostomy tube, i.e., from the proximal to the distal ends thereof, with sectional flexibility sufficient to bend to the curvature of the tracheostomy tube without inducing undue frictional engagement of the wall of the tracheostomy tube. The obturator of the invention possesses a handle at its proximal end that allows it to be inserted and removed from a cannula. It also possesses a plurality of protrusions, extending from its centered elongated longitudinal axis, that make contact with the interior wall of the tracheostomy tube when the obturator is inserted in the tracheostomy tube. The protrusions serve to support enough of the cylindrical wall of the tracheostomy tube so that the tube can be inserted into the trachea passage. The distal end of the obturator possesses means for non abrasively blocking the distal end of the tracheostomy tube within which it is situated. In addition, the invention relates to a flexible obturator lodged within a tracheostomy tube possessing flexible walls.

The invention relates to a flexible obturator of a length sufficient to allow it to extend the length of a tracheostomy tube, i.e., from the proximal to the distal ends thereof, and curving to the shape of the tracheostomy tube. The obturator possesses a handle at its proximal end and a tip at its distal end, and a plurality of interbonded protrusions. The protrusions in one embodiment would be non-bendable and would be separated by a flexible bending section that would be free to bend in two planes. The protrusions may be molded along with the flexible shaft section, or may be attached as separate parts that are assembled together. The second embodiment has protrusions that flex in one plane. The obturator would have a plurality of these protrusions placed at fight angles to one another along the central axis of the device to give the ability to bend in the two orthogonal planes. Each protrusion in the second embodiment would contact the walls at its edges, and would have the ability to incrementally bend in one plane through the flat section of the protrusion. Since the protrusions and the flexible sections are combined into one feature, the complex two plane bending comes from the incremental bending of the orthography mounted protrusions to yield the two degrees of freedom in bending. The protrusions could resemble small disk shapes that are bounded at fight angles to one another along the central axis, or could be molded as a complex shape in one operation. The distal end of the obturator possesses means for smooth entry of the tracheostomy tube within which it is situated into the trachea. The invention relates to a flexible obturator lodged within a tracheostomy tube possessing flexible walls.

This invention encompasses an obturator that is bendable and normally straight when not present in a tracheostomy tube. In such a state, the centered elongated longitudinal axis of the obturator is normally straight, meaning that its axis is essentially devoid of curvature in any direction. When the straight obturator is inserted into a tracheostomy tube possessing a curved shape, the obturator bends and conforms to the curvature of the tracheostomy tube. That means that the centered elongated longitudinal axis curves in conformation with the curvature of the tracheostomy tube.

The obturator possesses protruding lateral extensions from the centered elongated longitudinal axis that are capable of contacting or essentially contacting the inner wall of the tracheostomy tube. These protruding lateral extensions act to support the wall of the tracheostomy tube and insure that the walls do not adversely bend or buckle. In addition, the protruding lateral extensions assure the fit of the obturator within the tracheostomy tube.

The obturator of the invention is provided with a smooth-surfaced distal end so that when the obturator is inserted into the tracheostomy tube, the smooth-surfaced distal end assists in entry of the tracheostomy tube into the trachea. In addition, the smooth-surfaced distal end of the obturator extends beyond the distal end opening of the tracheostomy tube. This minimizes the trauma that can be caused by the distal end of the tracheostomy tube on entry into the trachea environment. In a preferred embodiment, the combination of the distal end of the tracheostomy tube and the smooth-surfaced distal end of the obturator forms an essentially smooth-surfaced and blunt end that can be easily moved within the trachea passage.

The obturator of the invention is made of one or more plastics that, when at the thickness of the obturator bendable shaft section, exhibit a flexibility characterized by a section modulus (EI of between about $1.10^{-5}$ to about $1.10^{-3}$ pounds-in$^2$. The bendable shaft section of the obturator may be a defined rod or combination of thin sections that have a thickness oriented in such a way as to define flex points along the axis of the obturator. Each flex point acts as an independent spring. These flex points or the mensions of the rod, coupled with the inherent flexibility of the plastic making up the structure of the obturator, determine the flexibility of the obturator. A flex point is formed at a segment of the obturator where bending is anticipated and the segment possesses at least a single dimension that does not exceed that of the rod. A rod is the portion of the obturator that circumscribes the centered elongated longitudinal axis of the obturator. The dimension of the rod is predicated on the physical properties of the plastic used in forming the obturator. If the plastic is highly flexible, e.g., an elastomer, then the flex point may be rather thick. If the plastic is extremely stiff, then the flex point should be rather thin.

The advantages of bendable shaft sections in the obturator should be apparent. In the case of an obturator made of a single bendable shaft, frictional engagement of the tip on insertion in the tracheostomy tube will invoke the formation of a single bow that is capable of frictionally engaging the tube wall. This makes entry of the obturator into the tracheostomy tube difficult unless the plastic it is made of possesses inherent slip, i.e., a low coefficient of friction The protrusions present on the obturator do not frictionally engage the tube wall in a manner that makes insertion and withdrawal within the tube a chore.

DETAILED DESCRIPTION OF THE INVENTION

Figure 1:
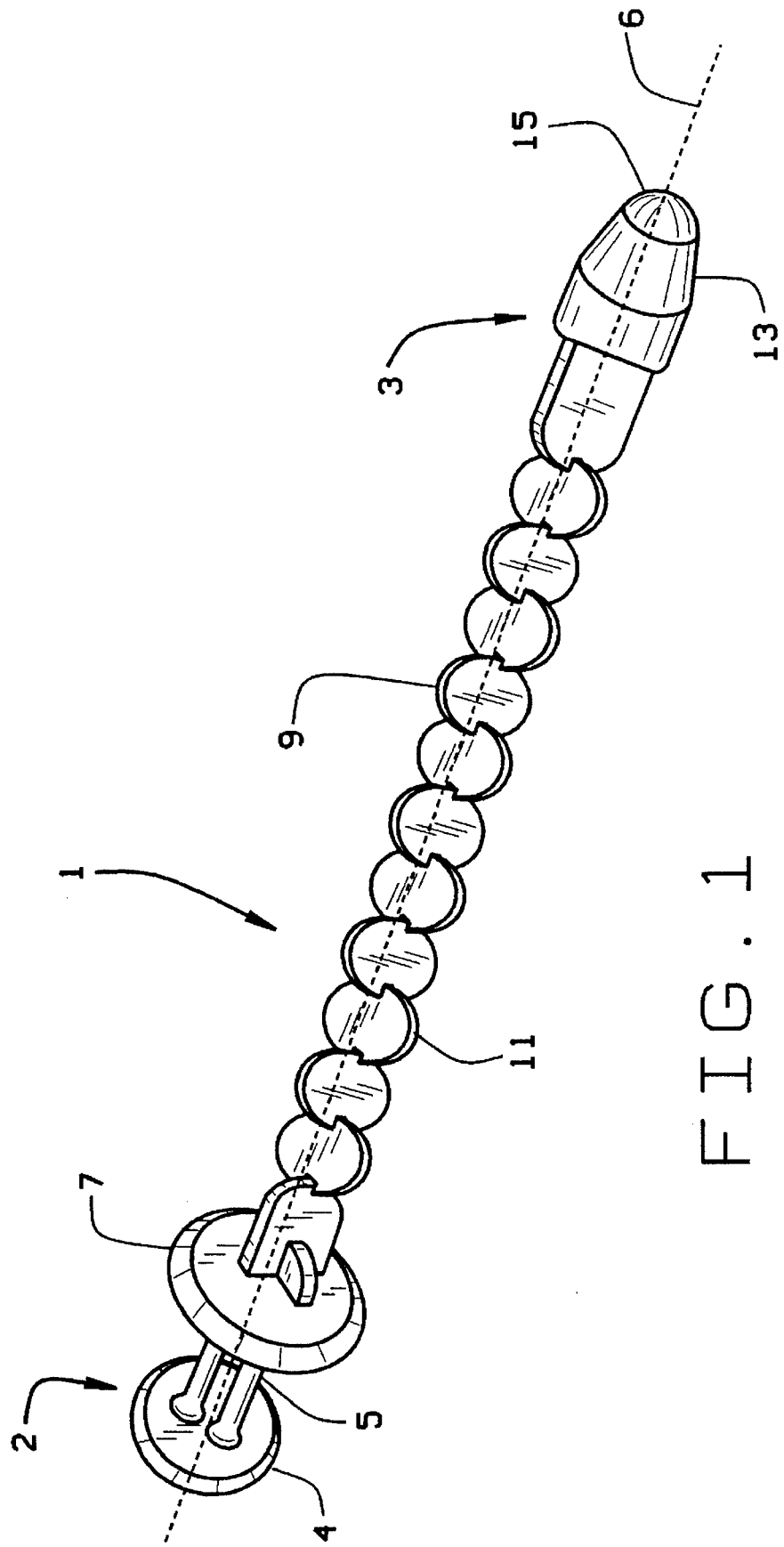
FIG. 1 is a perspective view of a preferred design for an obturator of the invention.

The obturator design of this invention combines structural support for the outer cannula when the outer cannula is made of flexible or soft material and requires such support, plus a design that incorporates flexibility so that the obturator can bend to match the shape of the outer cannula and respond to pressure exerted on the outer cannula during insertion into the tracheal opening while minimizing adverse frictional engagement.

These features make the obturator particularly desirable for use in tracheostomy devices designed for all uses, such as adult, neonatal and pediatric tracheotomy applications. Commercially important is the fact that the obturators of the invention can be made by injection molding of commercially available plastics. However, as will be appreciated, the obturators can also be made by other molding procedures or by hand sculpting of a block of a solid plastic or thermoset resin material.

The obturator designs of this invention may be bent and/or twisted so that they adapt effectively to changes in the shape and curvature of the outer cannula of the tracheostomy tubes in which they are employed. However, the degree to which the obturator of the invention may be twisted is limited by the degree of torque that the materials of construction used in making the obturator can withstand. The principles of construction of the obturator are simple. The obturator contains a handle portion at its proximal end that is used for inserting or withdrawing "the outer cannula supporting body" of the obturator into or from the outer cannula. The outer cannula supporting body is affixed to the handle and is capable of totally residing within the outer cannula. The distal end of the obturator is that portion of the obturator that is capable of being included within the distal end opening of the outer cannula. The combination of the distal ends of the obturator and the outer cannula form a relatively smooth surface that allows comfortable insertion of the tracheostomy tube into the trachea opening. Preferably, the distal end of the obturator is a bullet-like shaped structure that mates with the wall of the outer cannula. The length of the outer cannula supporting body of the obturator is defined by a longitudinal axis extending from the obturator's distal end to the handle. That length is characterized by separated flex points and separated protruding lateral extensions from the centered elongated longitudinal axis of the outer cannula supporting body of the obturator. As pointed out above, the lateral extensions are capable of contacting or essentially contacting the inner wall of the tracheostomy tube (outer cannula). These protruding lateral extensions act to support the wall of the tracheostomy tube and insure that the walls do not adversely bend or buckle. In addition, the protruding lateral extensions assure tight fit of the obturator within the tracheostomy tube even though the obturator is relatively easy to insert into or withdraw from the outer cannula.

The invention is more easily described by reference to the drawings. It is not the intention to limit the scope of the invention to the drawings. The drawings serve to teach the invention and give varied, but not limiting, illustrations of how the invention can be carried out.

Figure 2:
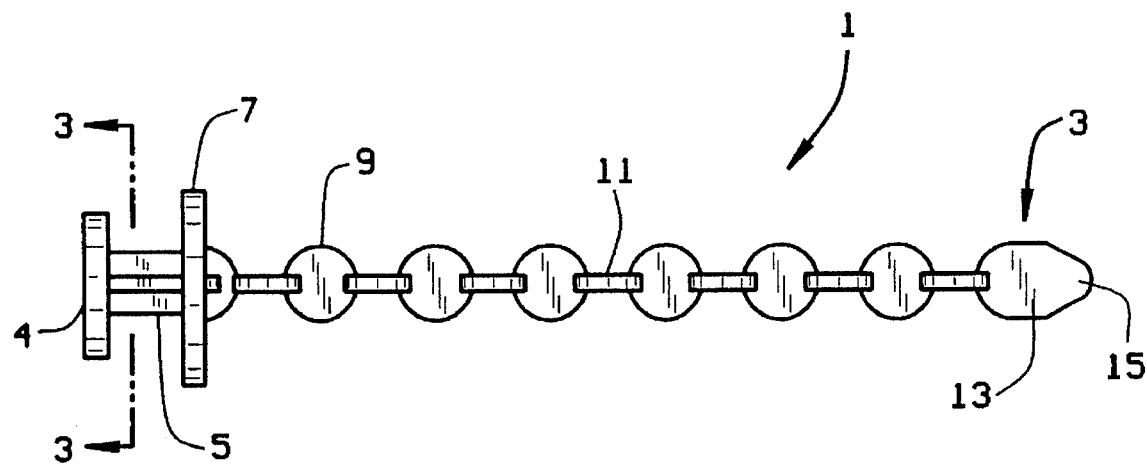
FIG. 2 is a side view of the obturator of FIG. 1.
Figure 3:
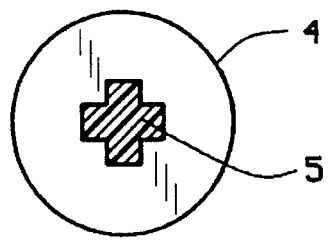
FIG. 3 is a cross-sectional view of the handle taken along lines A—A.

FIGS. 1, 2 and 3 illustrates a preferred obturator design for the practice of this invention. The obturator of FIGS. 1 and 2 contains a handle 2 at its proximal end, a bullet-like tip 3 at its distal end, and an outer cannula supporting body 1 between the proximal and distal ends, preferably all centrally circumscribing the longitudinal axis 6. It is not important to the invention that handle 2 centrally circumscribe longitudinal axis 6. In some embodiments of the invention, even outer cannula supporting body 1 need not centrally circumscribe the longitudinal axis 6. It is difficult to perceive of a construction where the tip 3 would not centrally circumscribe longitudinal axis 6.

Figure 11:
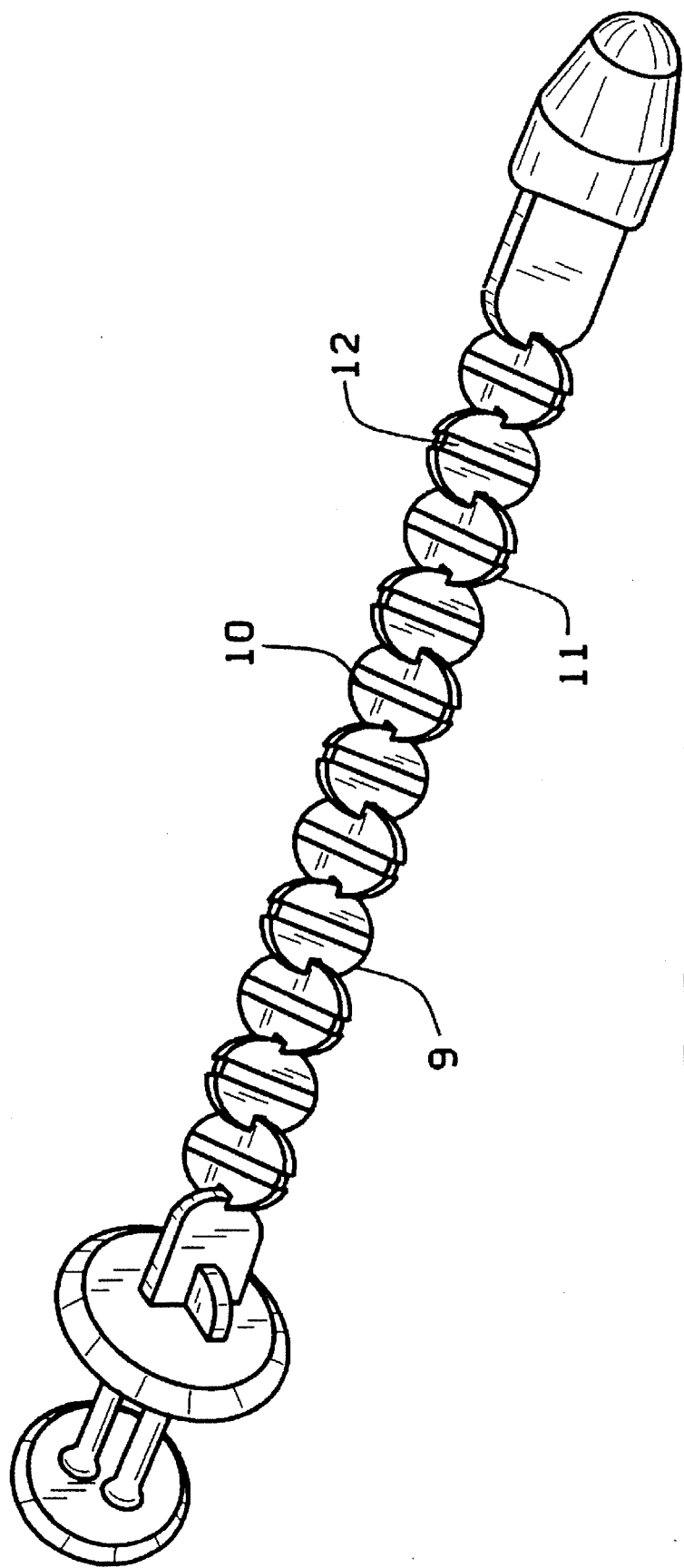
FIG. 11 is the same as FIG. 2 except that it contains grooves in discs 9 and 11.

As shown in FIGS 1 and 2, the outer cannula supporting body 1 is a alternating linear sequence of thin disc-like members 9 and 11 that are interbonded at perimeter points of each disc component. Each disc may have a thickness of about 0.3 to 2.5 millimeters, preferably from about 0.5 to 1.5 millimeter, depending upon the application for which the obturator is designed. That thickness coupled with the modulus of the plastic from which the disc is made will determine the extent to which each disc can be bent when inserted into an outer cannula. Disc-like member 9 is shown in a vertical state and disc-like member 11 is shown in a horizontal state, one being an angle of 90° of the other. The members need not be simply in vertical and horizontal states. They may be arranged as alternating discs at 45° angles to each adjacent disc. However, when so arranged, it is preferable that there be twice the number of such disc-like members to assure effective support for the outer cannula. The interbonded discs 9 and 11 are formed as part of formation of the whole obturator 1 by conventional injection molding. Each disc may be made with transversing grooves 10 and 12, as shown in FIG. 11, matched on each side so as to reduce the thickness of the disc at points along the length of the disc. This aids the flexibility of the disc and the obturator. Each disc 9 and 11 and their bond is formed in the injection mold.

Figure 10:
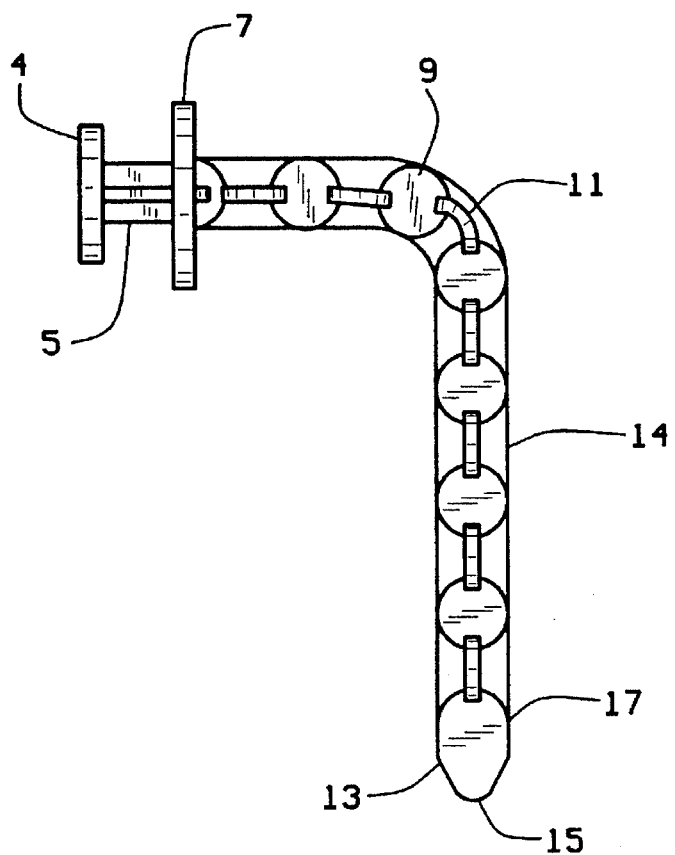
FIG. 10 is a schematic, cross-sectional side view of the obturator situated within an outer cannula of a tracheostomy device, encompassed by the invention.

The bullet-like distal tip 3 comprises sidewall 13 terminating at tip 15. Sidewall 13 slopes toward tip 15 resulting in a bullet-like shape that allows the obturator to be inserted into an outer cannula and providing a barrier (if a barrier is desired) to the distal opening of the outer cannula. If desired, the tip may be provided with a lumen or a series of lumens (not shown) to assist in air passage to the patient during insertion of the tracheostomy tube. As shown in FIG. 10, tip 15 in combination with the shape of the outer cannula forms a smooth surface at the distal end of the outer cannula. Distal tip 3 is made of the same plastic as the remainder of obturator 1.

FIG. 3 is a cross-sectional view of handle 2, taken along line A—A. It shows the four-leaf clover shape of handle section 5 and back wall 4. Not shown in FIG. 3 is forward wall 7 which acts a stop when inserting the obturator into an outer cannula's proximal end. This is illustrated in FIG. 10. The design of handle 2 allows the care giver to slide two adjacent fingers over handle section 5 and pull against back wall 4 to withdraw the obturator from the outer cannula, or push the obturator into the outer cannula by applying pressure on forward wall 7 while inserting tip 15 into the proximal opening of the outer cannula.

The obturator of the invention is preferably made of a thermoplastic resin such as polyolefins, ABS (acrylonitrile-1,4-butadiene-styrene random or block copolymers), polybutene, polystyrene, and the like. Preferred are the polyolefins such as polyethylene (high and low density versions), polypropylene, copolymers of ethylene and higher olefins, and the like.

Figure 4:
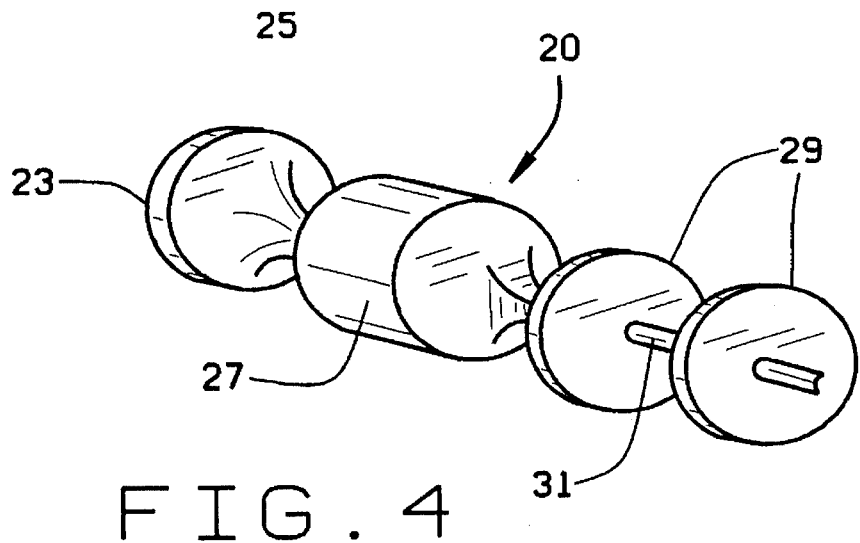
FIG. 4 is a perspective sectional view of an obturator encompassed by the invention.
Figure 8:
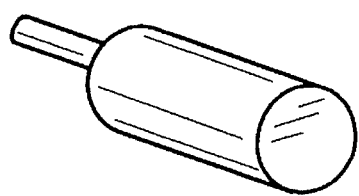
FIG. 8 illustrates the blunt distal end of the obturator of the invention.

FIG. 4 represents another shape of obturator. In this case, FIG. 4 shows the handle and part of the outer cannula supporting body. Obturator 20 contains a back wall 23 to the grip section 25 of the handle. The front wall 27 of the handle is capable of fitting within the proximal opening of the outer cannula, as contrasted with handle 2 where front wall 7 has a diameter greater than the proximal opening of the outer cannula. The outer cannula supporting body of obturator 20 comprises sectionalized rod 31 that directly connects with front wall 27. As shown in FIG. 8, a section of rod 31 affixes to the distal bullet-like tip 43 containing rounded tip section 41. In the case of obturator 20, each sectionalized rod 31 provides an independent flexibility, and the combination of the sections 31 provide the desired flexibility for insertion into an outer cannula. Each disc 29 is mounted so as to traverse the direction of rod 31. The cylindrical flat discs 29 essentially match the interior diameter of the outer cannula into which obturator 20 is to be fitted. There should be sufficient space between the outer peripheries of discs 29 and the interior wall of the outer cannula.

Figure 5:
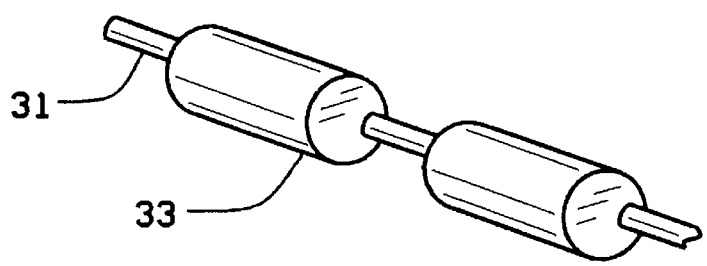
FIGS. 5, 6, 7 and 9 are different rod and projection designs for making the obturator of the invention.
Figure 6:
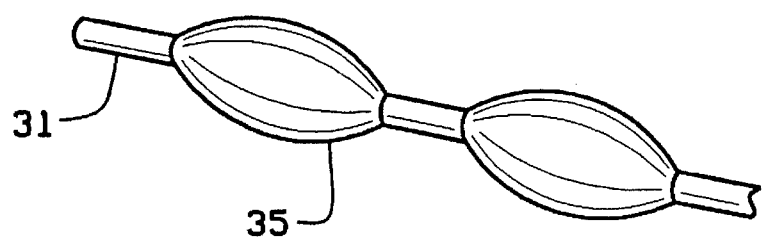
Figure 7:
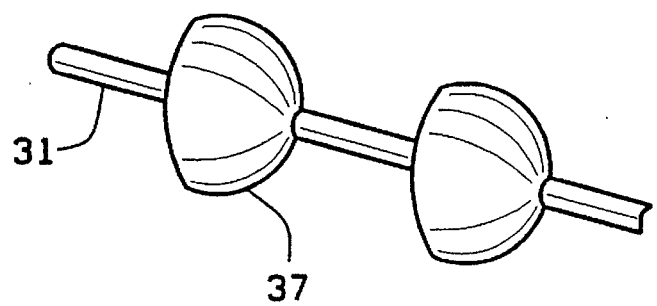
Figure 9:
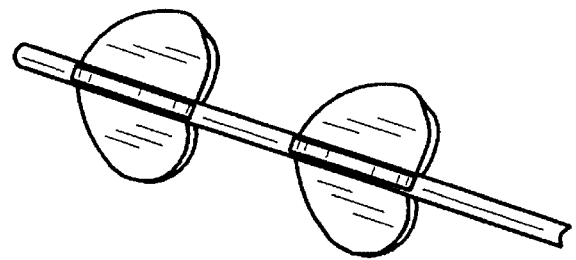

FIG. 5 provides another shaped outer cannula supporting body. In this case, a sectionalized rod 31, as in FIG. 4, is affixed to the handle at one end and another section to the tip at the other end. Instead of discs, this design uses spaced apart sectionalized cylinders 33 to support the obturator wall. FIG. 6 uses spaced apart oblong spacers 35; FIG. 7 uses spaced apart spherical spacers 37; and FIG. 9 uses sets of spaced apart parallel fins 39 mounted around rod 31 at 120° angles.

FIG. 10 illustrates, by a cross-sectional view, a schematic version of the preferred obturator of FIGS. 1–3, nestled in an outer cannula 14 containing tapered distal end 17 that terminates at the distal opening of the outer cannula 14. The combination of tapered end 17 and the smooth curved surface of the tip 15 of the obturator allows a non-abrasive insertion of the outer cannula containing the obturator into a trachea opening and the trachea. Where the outer cannula is made of a flexible plastic, the combination of an outer cannula with a tapered distal end and the rounded bullet-like tip of the flexible obturator of the invention allows easy introduction of the tracheostomy tube into the trachea.

The outer cannula may be made of conventional materials such as polyvinyl chloride, polyethylene, polypropylene, and the like plastics. However, owing to the flexibility that can be incorporated into a tracheostomy tube because of the reinforcing and flexing capabilities of the obturators of the invention, it is desirable to make the outer cannula of a flexible plastic, such as more highly plasticized polyvinyl chloride (typically comparable to the plasticized PVC used for making an inner cannula. Other flexible plastics may be employed, such as polyurethane elastomers, polybutene elastomers, ABS elastomers, and the like.

We claim:

1. A plastic obturator suitable for use in a tracheostomy tube comprising a handle at its proximal end, a bullet shaped tip at its distal end, and an outer cannula supporting body between the handle and the tip, which outer cannula supporting body contains sectionalized flex points and sectionalized laterally extending supporting surfaces along its length; wherein the laterally extending supporting surfaces are provided by a series of alternating flat discs positioned at different angles and one or more sets of alternating flat discs provide the sectionalized flex points.

2. The plastic obturator of claim 1 wherein the distance across the laterally supporting surfaces is approximately the inner diameter of a tracheostomy tube into which the obturator is usable.

3. The plastic obturator of claim 1 wherein the laterally extending supporting surfaces contain grooves in them.

4. The plastic obturator of claim 1 wherein the alternating flat discs are arranged along a longitudinal axis of the obturator and present edges that extend laterally of the axis.

5. The plastic obturator of claim 4 wherein the thickness of the flexible discs providing the flex points allows the obturator to be flexed upon entry to an outer cannula.

6. The plastic obturator of claim 4 wherein the discs contain grooves within their outer flat surfaces.

7. The plastic obturator of claim 4 wherein each adjacent disc is aligned about ninety degrees from the other.

8. A tracheostomy tube containing a plastic obturator, said plastic obturator comprising:

a handle at its proximal end;

a bullet shaped tip at its distal end; and an outer cannula supporting body between the handle and the tip, which outer cannula supporting body contains sectionalized flex points and sectionalized laterally extending supporting surfaces along its length;

wherein the laterally extending supporting surfaces are provided by a series of alternating flat discs positioned at different angles and one or more sets of alternating flat discs provide the sectionalized flex points.

9. The tracheostomy tube of claim 8 wherein the inner diameter of said tracheostomy tube is roughly equivalent to the outer diameter of said laterally extending supporting surfaces.

* * * * *